United States Patent
Marrocco et al.

(10) Patent No.: US 10,010,403 B2
(45) Date of Patent: Jul. 3, 2018

(54) STENT-GRAFT PROSTHESIS AND METHOD OF MANUFACTURE

(71) Applicant: Medtronic Vascular, Inc., Santa Rosa, CA (US)

(72) Inventors: Joseph Marrocco, Irvine, CA (US); Mathew Haggard, Santa Rosa, CA (US); Keith Perkins, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/131,511

(22) Filed: Apr. 18, 2016

(65) Prior Publication Data
US 2017/0296325 A1 Oct. 19, 2017

(51) Int. Cl.
*A61F 2/06* (2013.01)
*A61F 2/07* (2013.01)
*A61F 2/88* (2006.01)

(52) U.S. Cl.
CPC .................. *A61F 2/07* (2013.01); *A61F 2/88* (2013.01); *A61F 2002/075* (2013.01); *A61F 2240/001* (2013.01); *A61F 2250/0067* (2013.01)

(58) Field of Classification Search
CPC ...... A61F 2/91; A61F 2/07; A61F 2/06; A61F 2/915; A61F 2/82
See application file for complete search history.

(56) References Cited

U.S. PATENT DOCUMENTS

| 4,969,890 A | 11/1990 | Sugita et al. |
| 5,282,824 A | 2/1994 | Gianturco |
| 5,370,691 A | 12/1994 | Samson |
| 5,425,710 A | 6/1995 | Khair et al. |

(Continued)

FOREIGN PATENT DOCUMENTS

| DE | 102014115856 | 5/2015 |
| WO | WO96/21404 | 7/1996 |

(Continued)

OTHER PUBLICATIONS

PCT/US2017/026958 "The International Search Report and the Written Opinion of the International Searching Authority" dated Jun. 21, 2017.

*Primary Examiner* — Jason-Dennis Stewart
(74) *Attorney, Agent, or Firm* — Medler Ferro; Woodhouse & Mills PLLC

(57) ABSTRACT

A stent-graft prosthesis includes a generally tubular outer PTFE layer, a generally tubular helical stent, a generally tubular inner PTFE layer, and a suture or fabric support strip. The outer PTFE layer defines an outer layer lumen. The helical stent is disposed within the outer layer lumen and defines a stent lumen. The inner PTFE layer is disposed within the stent lumen and defines an inner layer lumen. The suture includes a suture first end coupled to a stent first end and a suture second end coupled to a stent second end, with the suture disposed between the outer PTFE layer and the inner PTFE layer. Alternatively, the fabric support strip is disposed between the outer and inner PTFE layers. The suture or fabric support strip may include a plurality of sutures or fabric support strips and may be spaced equally around a circumference of the inner PTFE layer.

15 Claims, 14 Drawing Sheets

(56) References Cited

U.S. PATENT DOCUMENTS

| | | | |
|---|---|---|---|
| 5,700,258 A | | 12/1997 | Mirigian et al. |
| 5,700,285 A | | 12/1997 | Myers |
| 5,735,892 A | | 4/1998 | Myers |
| 6,124,523 A | * | 9/2000 | Banas ........................ A61F 2/07 606/191 |
| 6,383,214 B1 | * | 5/2002 | Banas ........................ A61F 2/07 623/1.13 |
| 6,537,201 B1 | | 3/2003 | Kasic, II et al. |
| 6,547,814 B2 | | 4/2003 | Edwin et al. |
| 6,673,103 B1 | | 1/2004 | Golds et al. |
| 7,377,937 B2 | | 5/2008 | Dolan |
| 2001/0039446 A1 | | 11/2001 | Edwin et al. |
| 2008/0154351 A1 | * | 6/2008 | Leewood .................. A61F 2/86 623/1.2 |
| 2014/0130965 A1 | | 5/2014 | Banks et al. |
| 2015/0196383 A1 | | 7/2015 | Johnson |

FOREIGN PATENT DOCUMENTS

| | | |
|---|---|---|
| WO | WO98/38947 | 9/1998 |
| WO | WO2003/057075 | 7/2003 |
| WO | WO2008027188 | 3/2008 |

\* cited by examiner

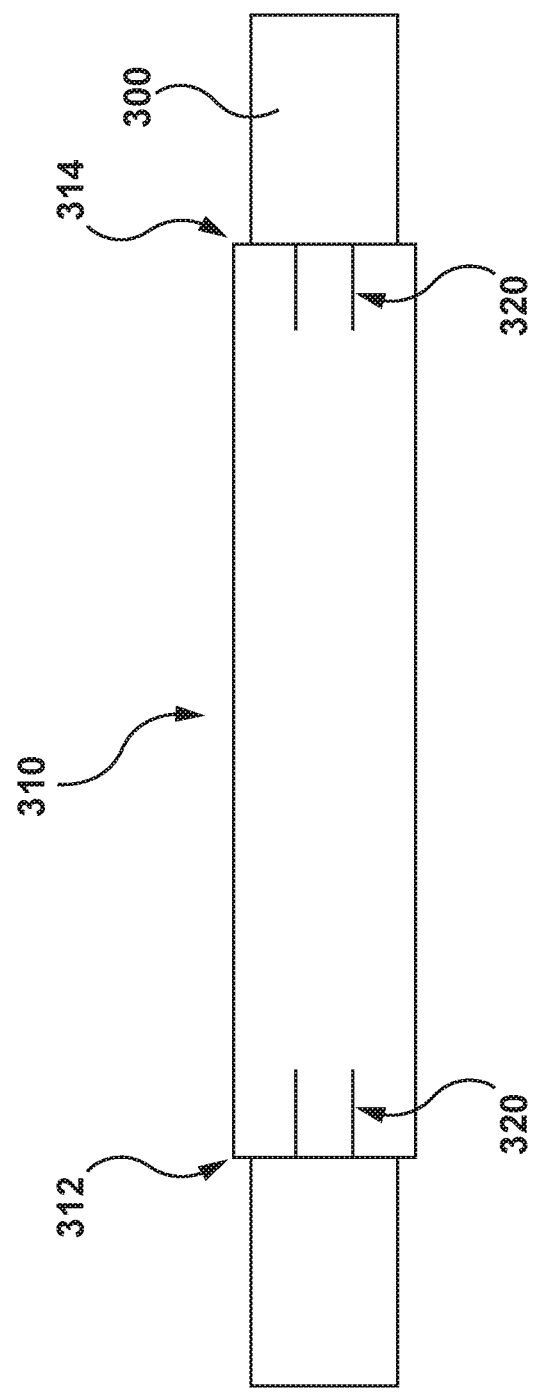

STENT-GRAFT PROSTHESIS AND METHOD OF MANUFACTURE

FIELD OF THE INVENTION

The present invention relates to an implantable prosthesis used to repair or replace a body lumen. More particularly, the present invention relates to an endoluminal prosthesis including a stent, inner and outer PTFE layers, and a support structure maintaining flexibility of the endoluminal prosthesis while providing increased tensile strength.

BACKGROUND

Endoluminal prostheses, also known as stent-graft prostheses, are medical devices commonly known to be used in the treatment of diseased blood vessels. A stent-graft prosthesis is typically used to repair, replace, or otherwise correct a damaged blood vessel. An artery or vein may be disease or damaged in a variety of different ways. The stent-graft prosthesis may therefore be used to prevent or treat a wide variety of defects such as stenosis of the vessel, thrombosis, occlusion, or an aneurysm.

Stents are generally tubular open-ended structures providing support for damaged, collapsing, or occluded blood vessels. They are radially expandable from a radially compressed configuration for delivery to the affected vessel site to a radially expanded configuration when deployed at the affected vessel treatment site, with the radially expanded configuration having a larger diameter than the radially compressed configuration. Stents are flexible, which allows them to be inserted through, and conform to, tortuous pathways in the blood vessels. Stents are generally inserted in the radially compressed configuration and expanded to the radially expanded configuration either through a self-expanding mechanism, or through the use of a balloon catheter. Helical stents are formed of a continuous, helically wound wire typically having a series of struts and apices, also known as crowns or bends. In some helical stents, connectors are disposed between adjacent bands of the helically formed wire.

A graft is another type of the endoluminal prosthesis, which is used to repair and replace various body vessels. Whereas the stent provides structural support to hold a damaged vessel open, a graft provides an artificial lumen through which blood may flow. Grafts are tubular devices that may be formed of a variety of materials, including textile, and non-textile materials. One type of non-textile material particularly suitable for use as an implantable prosthesis is polytetrafluoroethylene (PTFE). PTFE exhibits superior biocompatibility and has a low thrombogenicity, which makes it particularly useful as vascular graft material in the repair or replacement of blood vessels. In vascular applications, the grafts are manufactured from expanded PTFE tubes. These tubes have a microporous structure that allows natural tissue ingrowth and cell endothelization once implanted in the vascular system. This contributes to long-term healing and patency of the graft.

Stents and graft may be combined to form a stent-graft prosthesis, providing both structural support and an artificial lumen through which blood may flow. A stent-graft prosthesis is particularly useful to isolate aneurysms or other blood vessel abnormalities from normal blood pressure, reducing pressure on the weakened vessel wall, thereby reducing the chance of vessel rupture while maintaining blood flow. A stent-graft prosthesis is placed within the aneurysmal blood vessel to create a new flow path and an artificial flow conduit through the aneurysm, thereby reducing the exertion of blood pressure on the aneurysm. The stent-graft prosthesis incorporates one or more radially expandable stent(s) to be radially expanded in situ to anchor the tubular graft to the wall of the blood vessel at sites upstream and downstream of the aneurysm. Thus, endovascular stent-graft prostheses are typically held in place by mechanical engagement and friction by the outward radial force imparted on the wall of the blood vessel by the self-expanding or balloon expandable stent.

As previously described, polytetrafluoroethylene (PTFE) is a polymeric material that is well suited for use as the graft material of a stent-graft prosthesis. It is known in the art to form a stent-graft prosthesis that includes an outer PTFE layer which covers or lines at least one stent, as described in, for example, U.S. Pat. No. 5,700,285 and U.S. Pat. No. 5,735,892 to Myers. It is also known in the art to form a stent-graft prosthesis that includes an inner PTFE layer, an outer PTFE layer positioned about the inner PTFE layer and at least one stent interposed or encapsulated between the inner and outer PTFE layers, as described in, for example, U.S. Pat. No. 6,673,103 to Golds et al. and U.S. Patent Publication No. 2014/0130965 to Banks et al.

The design of a stent-graft prosthesis must balance strength and flexibility. Generally, increasing the strength a stent-graft prosthesis reduces its flexibility. Conversely, increasing the flexibility of stent-graft prosthesis generally decreases its strength. A stent-graft prosthesis formed with a helical stent without connectors and a PTFE graft material is generally highly flexible, but generally provides little support from either the helical stent or the fused PTFE layers when the stent-graft prosthesis is in tension. As the stent-graft prosthesis encounters tension during use or insertion within a delivery system, durability issues of the PTFE layers can occur. During the periods of tension, the stent-graft prosthesis elongates and the PTFE layers can tear. Pull-loading of a stent-graft prosthesis of this kind into a delivery system is therefore difficult and potentially damaging to the stent-graft prosthesis. Thus, the surgical team will often resort to push-loading of the stent-graft prosthesis into the delivery system. However, push-loading of the stent-graft prosthesis can result in train-wrecking issues causing damage to the stent-graft prosthesis.

Accordingly, there is a need for an improved stent-graft prosthesis design providing additional strength when the stent-graft prosthesis is under tension while maintaining flexibility, and methods for manufacturing such a stent-graft prosthesis.

SUMMARY OF THE INVENTION

Embodiments hereof relate to a stent-graft prosthesis for implantation within a blood vessel. The stent-graft prosthesis includes a generally tubular outer PTFE layer, a generally tubular helical stent, a generally tubular inner PTFE layer, and a suture. The outer PTFE layer defines an outer layer lumen. The helical stent is disposed within the outer layer lumen, includes a stent first end and a stent second end, and defines a stent lumen. The inner PTFE layer is disposed within the stent lumen and defines an inner layer lumen. The suture includes a suture first end coupled to the stent first end and a suture second end coupled to the stent second end. The suture is disposed between the outer PTFE layer and the inner PTFE layer.

Embodiments hereof also relate to a stent-graft prosthesis for implantation within a blood vessel. The stent-graft prosthesis includes a generally tubular outer PTFE layer, a generally tubular helical stent, a generally tubular inner PTFE layer, and a fabric support strip. The outer PTFE layer defines an outer layer lumen. The helical stent is disposed within the outer layer lumen and defines a stent lumen. The inner PTFE layer is disposed within the stent lumen and includes a first end and a second end, and defines a central passage and a central axis. The fabric support strip is encapsulated between the outer PTFE layer and the inner PTFE layer, and extends generally longitudinally from a first end of the stent-graft prosthesis to a second end of the stent-graft prosthesis.

Embodiments hereof also relate to a method of manufacturing a stent-graft prosthesis for implantation within a blood vessel. An inner PTFE layer is positioned over a mandrel. A first end of a suture is coupled to a first end of a helical stent and a second end of the suture is coupled to a second end of the helical stent such that the suture extends from the stent first end to the stent second end of a helical stent. The helical stent is positioned onto the inner PTFE layer. An outer PTFE layer is positioned over the helical stent and the inner PTFE layer. A heat shrink material is positioned over the outer PTFE layer, with the heat shrink material fully covering the inner and outer PTFE layers. The inner and outer PTFE layers are heated to couple together the inner and outer PTFE layers such that the inner PTFE layer, the helical stent, the suture, and the outer PTFE layer to form the stent-graft prosthesis. The heat shrink material is removed from the stent-graft prosthesis. The stent-graft prosthesis is removed from the mandrel.

Embodiments hereof also relate to a method of manufacturing a stent-graft prosthesis for implantation within a blood vessel. An inner PTFE layer is positioned over a mandrel. A helical stent is positioned onto the inner PTFE layer. A fabric support strip is positioned over the inner PTFE layer. An outer PTFE layer is positioned over the fabric support strip, helical stent, and inner PTFE layer. A heat shrink material is positioned over the outer PTFE layer, with the heat shrink material fully covering the inner and outer PTFE layers. The inner and outer PTFE layers are heated to couple together the inner and outer PTFE layers such that the inner PTFE layer, the helical stent, the fabric support strip, and the outer PTFE layer to form the stent-graft prosthesis. The heat shrink material is removed from the stent-graft prosthesis. The stent-graft prosthesis is removed from the mandrel.

BRIEF DESCRIPTION OF DRAWINGS

FIGS. 9-14 are simplified illustrations of the steps in an embodiment of a method of manufacturing the stent-graft prosthesis of FIG. 1.

DETAILED DESCRIPTION

Specific embodiments of the present invention are now described with reference to the figures, wherein like reference numbers indicate identical or functionally similar elements. The following detailed description is merely exemplary in nature and is not intended to limit the invention or the application and uses of the invention. Although the description of the invention is in the context of a stent-graft prosthesis and a method of manufacturing a stent-graft prosthesis for the treatment of blood vessels, the invention may also be used and manufactured for use in any body passageways where it is deemed useful. Furthermore, there is no intention to be bound by any expressed or implied theory presented in the preceding technical field, background, brief summary, or the following detailed description.

Figure 1:
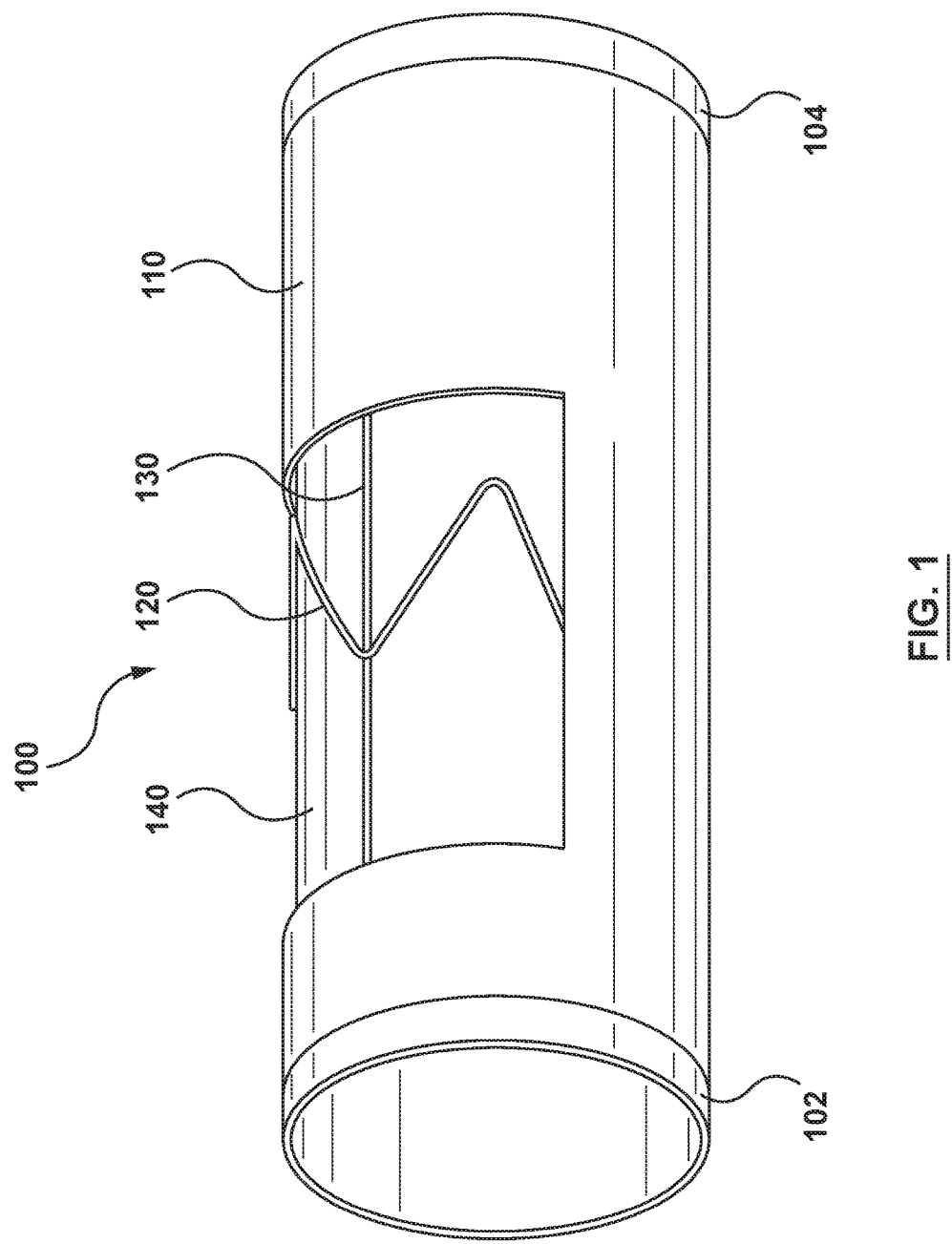
FIG. 1 is a perspective illustration with partial cutaway of an embodiment of a stent-graft prosthesis according to an embodiment hereof.
Figure 2:
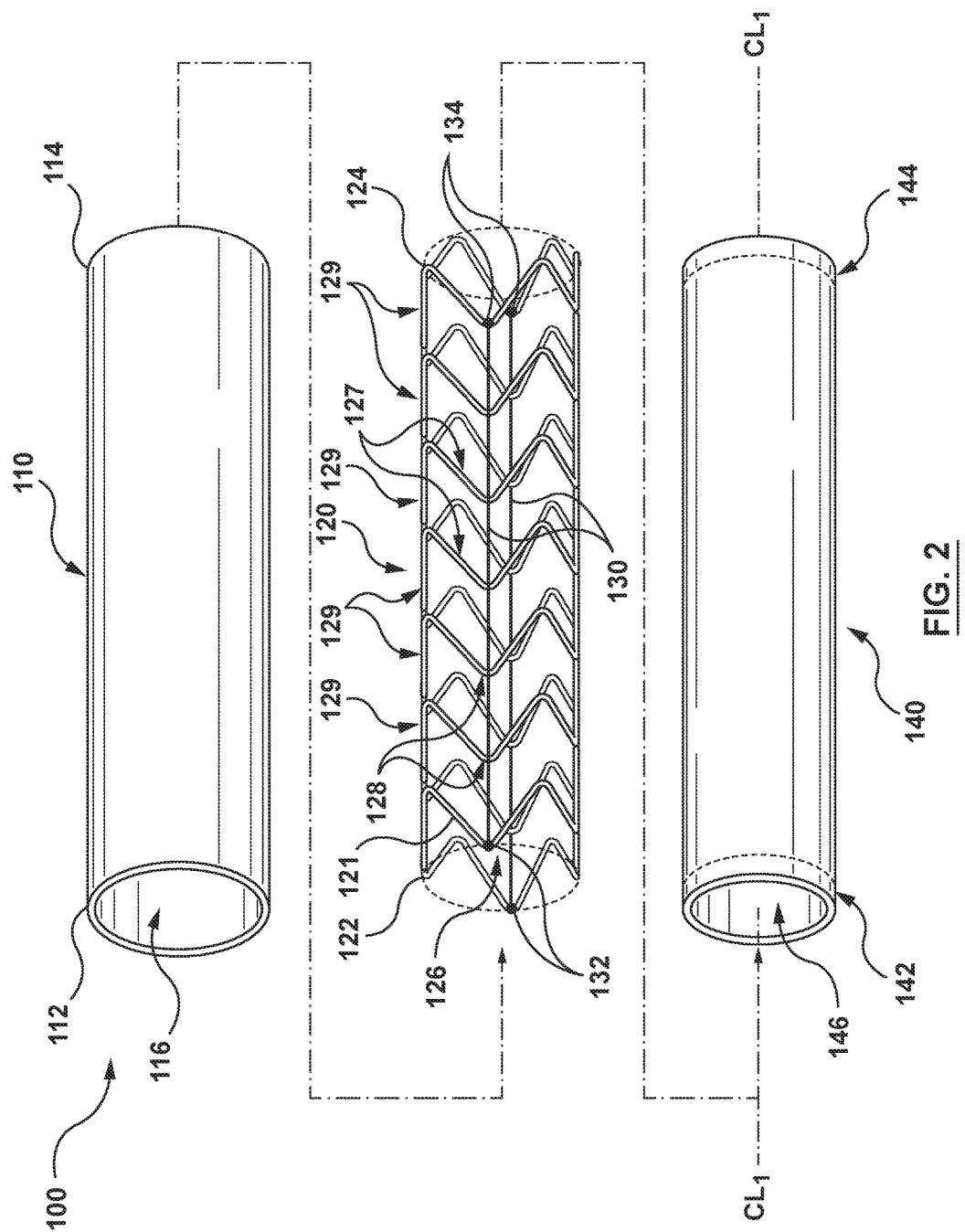
FIG. 2 is an exploded perspective illustration of the stent-graft prosthesis of FIG. 1.
Figure 3:
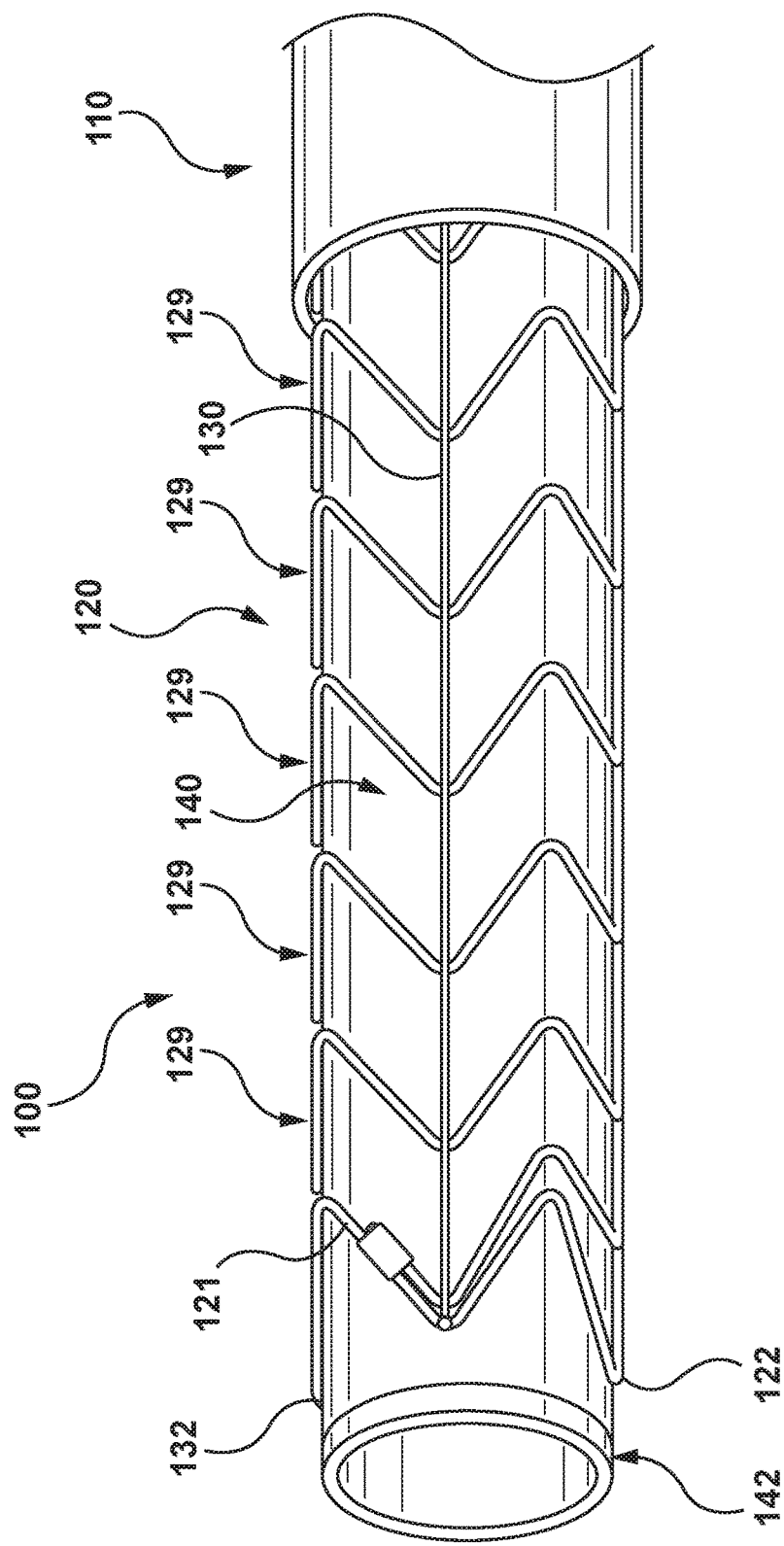
FIG. 3 is a partial cutaway perspective illustration of the stent-graft prosthesis of FIG. 1.

A stent-graft prosthesis according to an embodiment of the present invention. Is shown in FIGS. 1-3. Stent-graft prosthesis 100 includes an outer PTFE layer 110, a helical stent 120, an inner PTFE layer 140, and a suture 130, as shown in FIG. 1. Components in accordance with the embodiment of stent-graft prosthesis 100 of FIG. 1 are presented in greater detail in FIGS. 2-3. The present disclosure is in no way limited to outer PTFE layer 110, helical stent 120, inner PTFE layer 140, and suture 130, shown and described below. Components of stent-graft prosthesis 100 may assume different forms and construction based upon application needs as described in greater detail in for example, U.S. Pat. No. 5,700,285 and U.S. Pat. No. 5,735,892 to Myers, U.S. Pat. No. 6,673,103 to Golds et al., and U.S. Patent Publication No. 2014-0130965 to Banks et al., previously incorporated herein. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Stent-graft prosthesis 100 is of a generally tubular configuration and includes a first end 102 and a second end 104, as shown in FIG. 1. Stent-graft prosthesis 100 includes a radially compressed configuration (not shown) for delivery to the affected site of a blood vessel and a radially expanded configuration, as shown in FIG. 1. Stent-graft prosthesis 100 may be self-expanding or balloon expandable.

Outer PTFE layer 110 is of a generally tubular configuration, includes a first end 112 and a second end 114, and defines an outer layer lumen 116 therein, as shown in FIG. 2. Outer PTFE layer 110 forms an exterior surface of stent-graft prosthesis 100. More particularly, outer PTFE layer 110 is configured to maintain helical stent 120, suture 130, and inner PTFE layer 140 therein, as shown in FIGS. 2-3 and described in greater detail below. While outer PTFE layer 110 is shown with a tubular shape, it is not meant to limit the design, and other shapes and sizes may be utilized. The length of outer PTFE layer 110 is approximately equal to the desired length of stent-graft prosthesis 100. Outer PTFE layer 110 can assume a variety of configurations described in greater detail in for example, U.S. Pat. No. 5,700,285 and U.S. Pat. No. 5,735,892 to Myers, U.S. Pat.

No. 6,673,103 to Golds et al., and U.S. Patent Publication No. 2014/0130965 to Banks et al., and previously incorporated herein. Outer PTFE layer 110 may be formed, for example, and not by way of limitation, of polytetrafluoroethylene (PTFE), expandable polytetrafluoroethylene (ePTFE), or any other material suitable for purposes of the present disclosure.

Helical stent 120 is of a generally tubular, open-ended structure and is disposed within outer layer lumen 116, as shown in FIGS. 2-3. Helical stent 120 includes a stent first end 122 and a stent second end 124, and defines a stent lumen 126 therein, as shown in FIG. 2. Helical stent 120 is radially expandable from a radially compressed configuration (not shown) for delivery to a radially expanded configuration when deployed, as shown in FIGS. 2-3. In some embodiments, helical stent 120 is formed of a continuous, helically wound wire 121 bent into a waveform having struts 127 and apices 128, also known as crowns or bends, as shown in FIG. 2. The waveform is then helically wrapped into a tubular form, as known in the art. The helically wrapped waveform forms bands 129 of helical stent 120. In the embodiment shown in FIGS. 2-3, adjacent bands 129 are not coupled to each other except through the continuation of wire 121, sutures 120 described below, and inner and outer PTFE layers 140, 110. In other words, additional stent structures do not couple together adjacent bands 129. However, as shown in FIG. 3, free ends of wire 121 (only one shown in FIG. 3) may be coupled to a strut 127, for example, using a crimp connector 123. Helical stent 120 yields a flexible, conformable helical stent, which expands uniformly and provides good radial strength, scaffolding, and fatigue characteristics when expanded. Helical stent 120 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

Inner PTFE layer 140 is of a generally tubular configuration, includes a first end 142 and a second end 144, and defines an inner layer lumen 146 and a central axis $CL_1$ therein, as shown in FIG. 2. Inner PTFE layer 140 forms an interior surface of stent-graft prosthesis 100. More particularly, inner PTFE layer 140 is configured to provide unrestricted blood flow through stent-graft prosthesis 100 when stent-graft prosthesis 100 is in the radially expanded configuration and deployed at a treatment site of a blood vessel. In some embodiments, the length of inner PTFE layer 140 may be greater than the desired length of stent-graft prosthesis 100. In such embodiments, inner PTFE layer 140 includes first and second ends 142, 144, which are folded over or cuffed during the manufacturing process, as will be explained in more detail herein. Thus, in some embodiments, the length of inner PTFE layer 140 is equal to the desired length of stent-graft prosthesis 100 plus first and second ends 142, 144. While inner PTFE layer 140 is shown with a generally tubular shape, it is not meant to limit the design, and other shapes and sizes are contemplated based on the application requirements. Inner PTFE layer 140 can assume a variety of configurations described in greater detail in for example, U.S. Pat. No. 5,700,285 and U.S. Pat. No. 5,735,892 to Myers, U.S. Pat. No. 6,673,103 to Golds et al., and U.S. Patent Publication No. 2014/0130965 to Banks et al., previously incorporated herein. Inner PTFE layer 140 may be formed, for example, and not by way of limitation, of polytetrafluoroethylene (PTFE), expandable polytetrafluoroethylene (ePTFE), or any other material suitable for purposes of the present disclosure.

Suture 130 is an elongated member and includes a suture first end 132 coupled to stent first end 122 and a suture second end 134 coupled to stent second end 124, as shown in FIGS. 2-3. Suture 130 provides additional tension strength to stent-graft prosthesis 100 as described in greater detail below. Suture 130 may be formed, for example, and not by way of limitation, of nylon, polybutester, polypropylene, silk, polyester or other materials suitable for the purposes described herein. Suture 130 may be coupled to helical stent 120, for example, and not by way of limitation, by tying, fusing, welding, or other methods suitable for the purposes described herein.

According to embodiments hereof, helical stent 120 is configured to be disposed within outer layer lumen 116 of outer PTFE layer 110, and inner PTFE layer 140 is configured to be disposed within stent lumen 126 of helical stent 120, as shown in FIGS. 2-3. Outer PTFE layer 110 is bonded to inner PTFE layer 140 for example, and not by way of limitation, by fusing, welding, adhesives, or other methods suitable for the purposes described herein.

Suture 130 is coupled to helical stent 120 as previously described and configured to extend generally longitudinally with respect to stent-graft prosthesis 100, as shown in FIGS. 2-3. Suture 130 is further configured to provide additional tensile strength to stent-graft prosthesis 100 by limiting the elongation of stent-graft prosthesis 100 when under tension. More particularly, suture 130, attached to helical stent 120 as previously described, limits elongation/stretching of helical stent 120, thereby limiting elongation/stretching of stent-graft prosthesis 100 and reducing the potential for damage to outer and inner PTFE layers 110/140 when stent-graft prosthesis 100 is under tension during use or insertion into a delivery device insertion, for example.

In the embodiment shown in FIGS. 2-3, two sutures 130 are shown spaced 180 degrees apart around the circumference of inner PTFE layer 140. However, this is not meant to limit the design, and more or fewer sutures 130 may be utilized. Further, sutures 130 need not be spaced equally about a circumference of inner PTFE layer 140.

Figure 4:
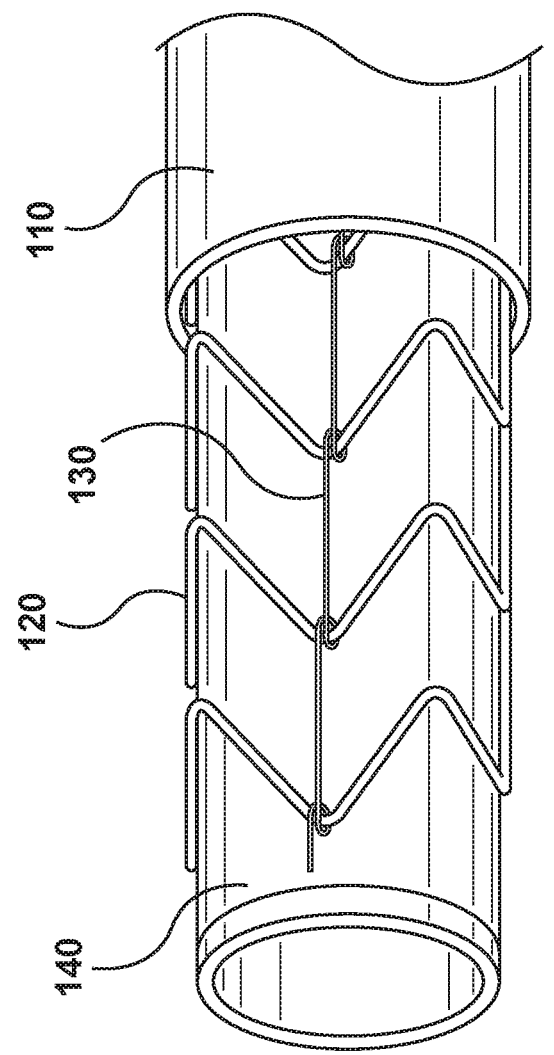
FIG. 4 is a perspective illustration of a suture wrapped around an apex of a helical stent of the stent-graft prosthesis of FIG. 1.

In the embodiment shown in FIGS. 2-3, sutures 130 are disposed between helical stent 120 and outer PTFE layer 110. However, this is not meant to limit the design and other configurations may be utilized. For example, and not by way of limitation, sutures 130 may be disposed between helical stent 120 and inner PTFE layer 140. Alternatively, sutures 130 may be woven over some portions of helical stent 120 (between helical stent 120 and outer PTFE layer 110) and under other portions of helical stent 120 (between helical stent 120 and inner PTFE layer 140. In another non-limiting example, shown in FIG. 4, sutures 130 may be wrapped around some of the apices 128 of helical stent 120 as sutures 130 extend along the length of helical stent 120.

In the embodiment shown in FIGS. 2-3, sutures 130 are coupled to first and second ends 122, 124 of helical stent 120 at stent apices 128. However, this is not meant to limit the design, and sutures may be coupled to other portions of helical stent, such as, but not limited to, struts 127.

Figure 5:
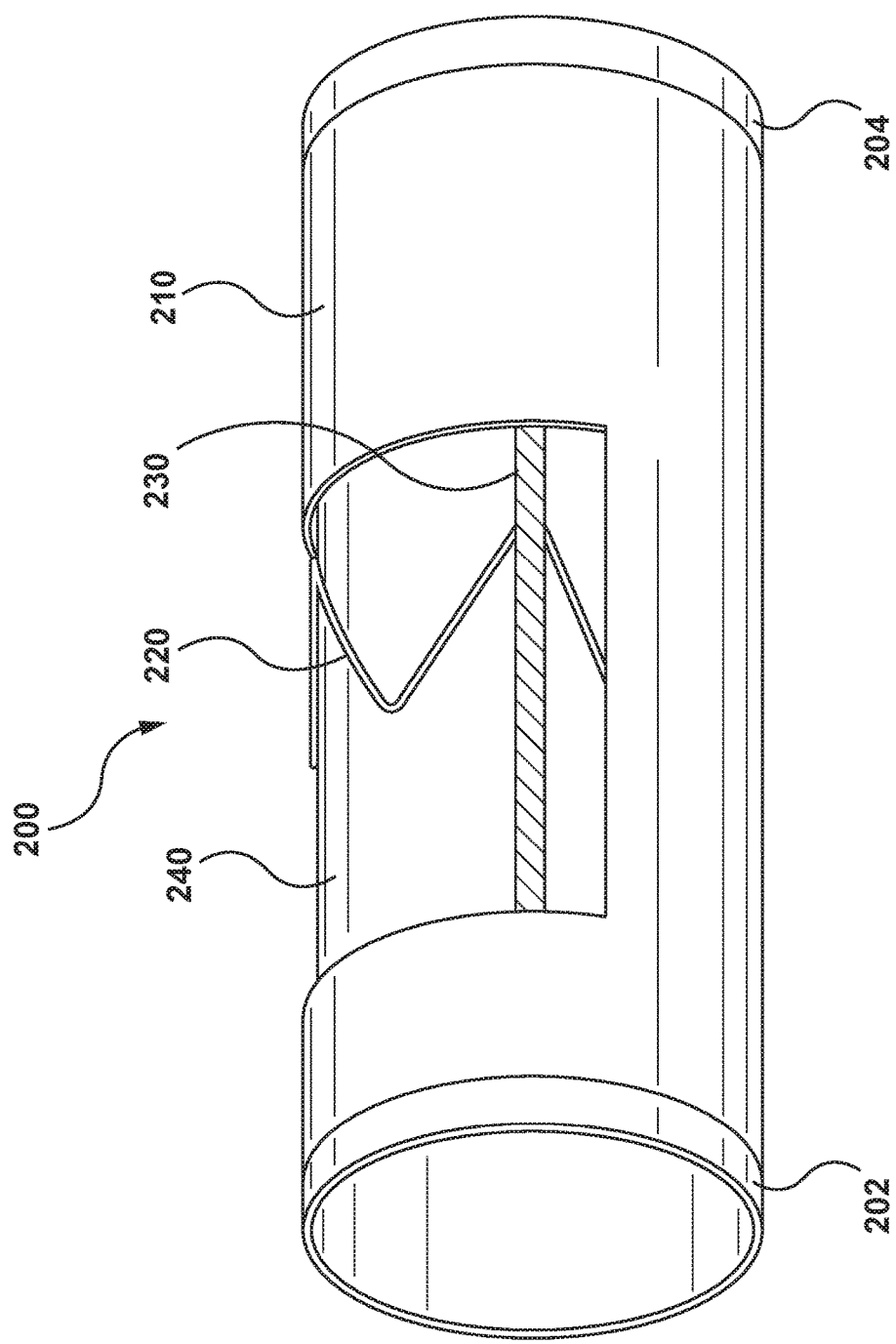
FIG. 5 is a perspective illustration with partial cutaway of a stent-graft prosthesis according to another embodiment hereof.

FIGS. 5-8 show a stent-graft prosthesis 200 according to another embodiment of the present disclosure. Stent-graft prosthesis 200 includes an outer PTFE layer 210, a helical stent 220, an inner PTFE layer 240, and a fabric support strip 230. Components in accordance with the embodiment of stent-graft prosthesis 200 of FIG. 5 are presented in greater detail in FIGS. 6-8. The present disclosure is in no way limited to outer PTFE layer 210, helical stent 220, inner PTFE layer 240, and fabric support strip 230, shown and described below. Components of stent-graft prosthesis 200 may assume different forms and construction based upon application needs as described in greater detail in for example, U.S. Pat. No. 5,700,285 and U.S. Pat. No. 5,735,892 to Myers, U.S. Pat. No. 6,673,103 to Golds et al., and U.S. Patent Publication No. 2014/0130965 to Banks et al., previously incorporated herein. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Stent-graft prosthesis 200 is of a generally tubular configuration and includes a first end 202 and a second end 204, as shown in FIG. 5. Stent-graft prosthesis 200 includes a radially compressed configuration (not shown) for delivery to the affected site of a blood vessel and a radially expanded configuration, as shown in FIG. 5. Stent-graft prosthesis 200 may be self-expanding or balloon expandable.

Figure 6:
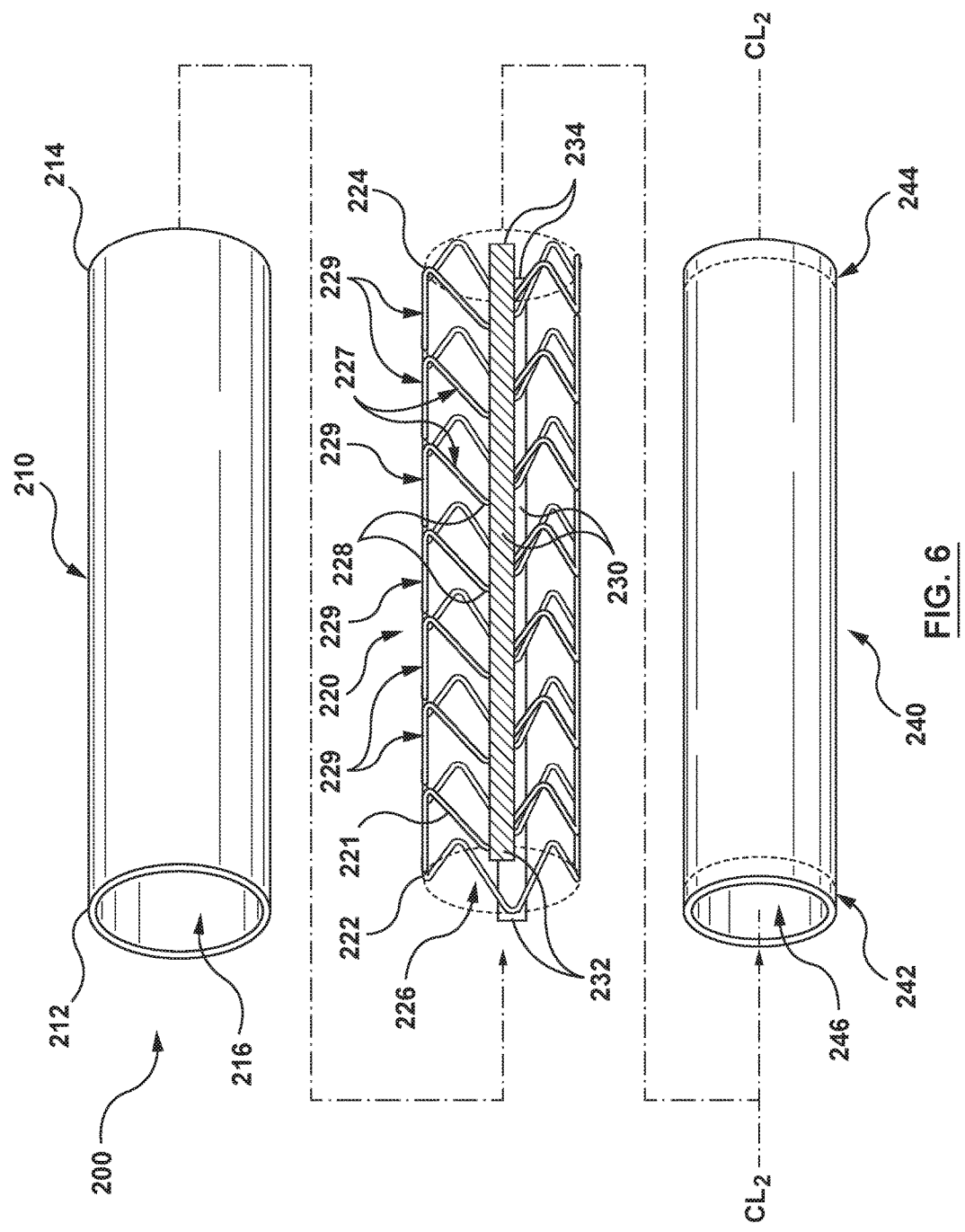
FIG. 6 is an exploded perspective illustration of the stent-graft prosthesis of FIG. 5.
Figure 7:
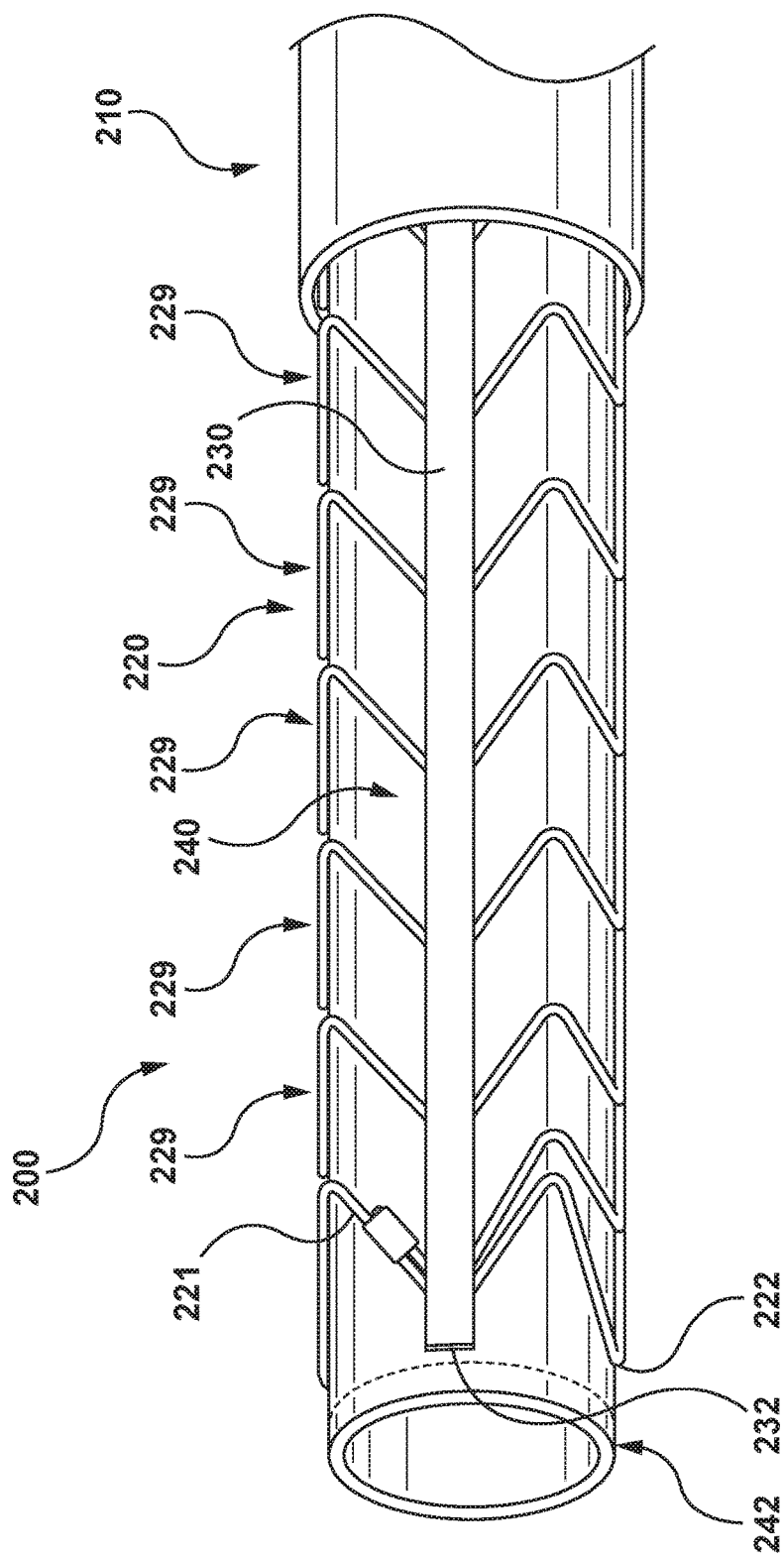
FIG. 7 is a partial cutaway perspective illustration of the stent-graft prosthesis of FIG. 5.

Outer PTFE layer 210 is of a generally tubular configuration, includes a first end 212 and a second end 214, and defines an outer layer lumen 216 therein, as shown in FIG. 6. Outer PTFE layer 210 forms an exterior surface of stent-graft prosthesis 200, More particularly, outer PTFE layer 210 is configured to maintain helical stent 220, fabric support strip 230, and inner PTFE layer 240 therein, as shown in FIGS. 6-7 and described in greater detail below. The length of outer PTFE layer 210 may be approximately equal to the desired length of stent-graft prosthesis 200. While outer PTFE layer 210 is shown with a tubular shape, it is not meant to limit the design, and other shapes and sizes may be utilized. Outer PTFE layer 210 can assume a variety of configurations described in greater detail in for example, U.S. Pat. No. 5,700,285 and U.S. Pat. No. 5,735,892 to Myers, U.S. Pat. No. 6,673,103 to Golds et al., and U.S. Patent Publication No. 2014/0130965 to Banks et al., previously incorporated herein. Outer PTFE layer 210 may be formed, for example, and not by way of limitation, of polytetrafluoroethylene (PTFE), expandable polytetrafluoroethylene (ePTFE), or any other material suitable for purposes of the present disclosure.

Helical stent 220 is of a generally tubular, open-ended structure and is disposed within outer PTFE layer lumen 216, as shown in FIGS. 6-7. Helical stent 220 includes a stent first end 222 and a stent second end 224, and defines a stent lumen 226 therein, as shown in FIG. 6. Helical stent 220 is radially expandable from a radially compressed configuration (not shown) for delivery to a radially expanded configuration when deployed, as shown in FIGS. 6-7. In some embodiments, helical stent 220 is formed of a continuous helically wound wire 221 bent into a waveform having struts 227 and apices 228, also known as crowns or bends, as shown in FIG. 6. The waveform is then helically wrapped into a tubular form, as known in the art. The helically wrapped waveform forms bands 229 of helical stent 220. In the embodiment shown in FIGS. 6-7, adjacent bands 229 are not coupled to each other except through the continuation of wire 221, fabric support strip 230 described below, and inner and outer PTFE layers 240, 210. In other words, additional stent structures do not couple together adjacent bands 229. However, as shown in FIG. 7, free ends of wire 221 (only one shown in FIG. 7) may be coupled to a strut 227, for example, using a crimp connector 223. Helical stent 220 yields a flexible, conformable stent, which expands uniformly and provides good radial strength, scaffolding, and fatigue characteristics when expanded. Helical stent 220 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

Inner PTFE layer 240 is of a generally tubular configuration, includes a first end 242 and a second end 244, and defines an inner layer lumen 246 and a central axis $CL_2$ therein, as shown in FIG. 6. Inner PTFE layer 240 forms an interior surface of stent-graft prosthesis 200. More particularly, inner PTFE layer 240 is configured to provide unrestricted blood flow through graft-stent prosthesis 200 when stent-graft prosthesis 200 is in the radially expanded configuration and deployed at a treatment site of a blood vessel. In some embodiments, the length of inner PTFE layer 240 may be greater than the desired length of stent-graft prosthesis 200. In such embodiments, inner PTFE layer 240 includes first and second ends 242, 244, which are folded over or cuffed during the manufacturing process as will be explained in more detail herein. Thus, in such embodiments, the length of inner PTFE layer 240 is equal to the desired length of stent-graft prosthesis 200 plus first and second ends 242, 244. While inner PTFE layer 240 is shown with a generally tubular shape, it is not meant to limit the design, and other shapes and sizes may be utilized. Inner PTFE layer 240 can assume a variety of configurations described in greater detail in for example, U.S. Pat. No. 5,700,285 and U.S. Pat. No. 5,735,892 to Myers, U.S. Pat. No. 6,673,103 to Golds et al., and U.S. Patent Publication No. 2014/0130965 to Banks et al., previously incorporated herein. Inner PTFE layer 240 may be formed, for example, and not by way of limitation, of polytetrafluoroethylene (PTFE), expandable polytetrafluoroethylene (ePTFE), or any other material suitable for purposes of the present disclosure.

Figure 8:
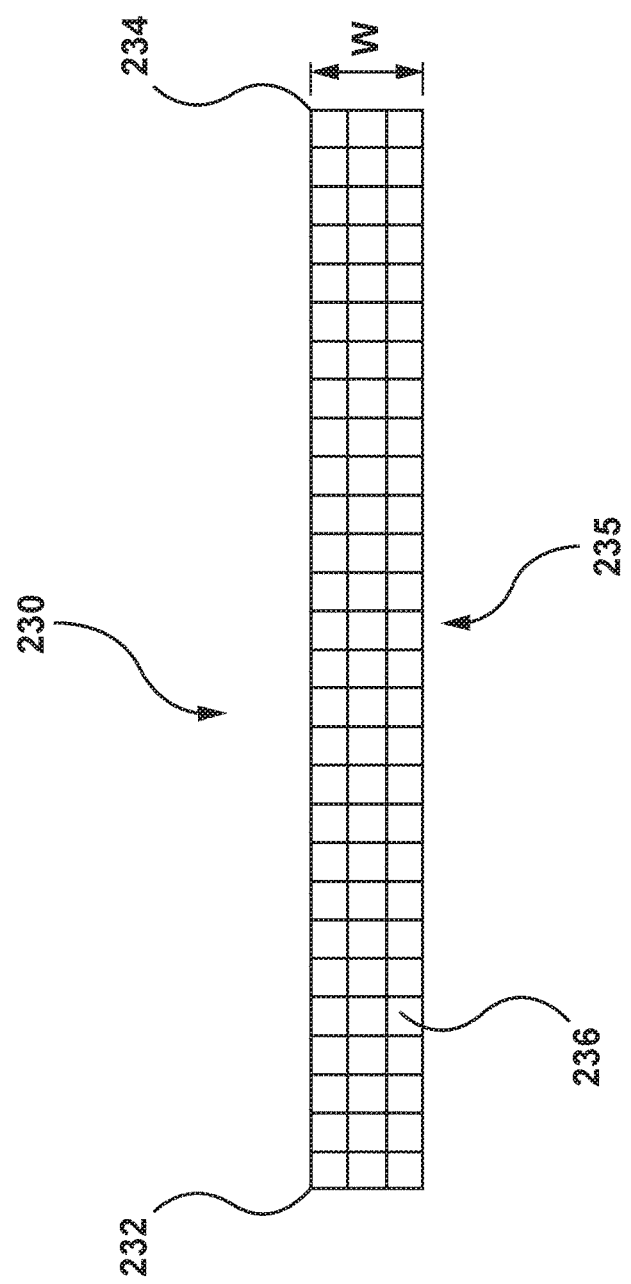
FIG. 8 is a side illustration of an embodiment of the fabric support strip of the stent-graft prosthesis of FIG. 5.

Fabric support strip 230 is an elongated member that provides additional tension strength to stent-graft 200 as described in greater detail below and shown in FIGS. 6-8. Fabric support strip 230 includes a strip first end 232 and a strip second end 234. In an embodiment, the length of fabric support strip 230 is approximately equal to the desired length of stent-graft prosthesis 200. Fabric support strip has a width W in the range of 0.5-8 mm, although other widths may also be used. As shown in FIG. 8, fabric support strip 230 may be a mesh fabric 235 including a plurality of openings 236 to improve bonding of outer PTFE layer 210 to inner PTFE layer 240 through fabric support strip 230. Fabric support strip 230 may be formed, for example, and not by way of limitation, of nylon, polybutester, polypropylene, silk, polyester or other materials suitable for the purposes described herein. Fabric support strip 230 may further include a biologically or pharmacologically active substance for example, and not by way of limitation, an antithrombogenic substance, a substance configured to increase endothelialization, an antineoplastic, an antimitotic, an anti-inflammatory, an antiplatelet, an anticoagulant, an anti-fibrin, an antithrombin, an antiproliferative, an antibiotic, an antioxidant, an antiallergic, or other substances or combinations of substances suitable for the purposes described herein.

According to embodiments hereof, helical stent 220 is configured to be disposed within outer layer lumen 216 of outer PTFE layer 210, and inner PTFE layer 240 is configured to be disposed within stent lumen 226 of helical stent 220, as shown in FIGS. 6-7. Outer PTFE layer 210 is bonded to inner PTFE layer 240 for example, and not by way of limitation, by fusing, welding, adhesives, or other methods suitable for the purposes described herein.

Fabric support strip 230 is configured to extend generally longitudinally with respect to stent-graft prosthesis 200, as shown in FIGS. 6-7. Fabric Support strip 230 is further configured to provide additional strength to stent-graft prosthesis 200 by limiting the elongation of stent-graft prosthesis 200 when under tension. More particularly, fabric support strip 230, bonded between outer PTFE layer 210 and inner PTFE layer 240, limits elongation/stretching of outer and inner PTFE layers 210/240 and helical stent 220, thereby limiting elongation/stretching of stent-graft prosthesis 200 and reducing the potential for damage to outer and inner PTFE layers 210/240 when stent-graft prosthesis 200 is under tension during use or insertion into a delivery device insertion, for example.

In the embodiment shown in FIGS. 6-7, two fabric support strips 230 are shown spaced 180 degrees apart around the circumference of inner PTFE layer 240. However, this is not meant to limit the design, and more for fewer fabric support strips 230 may be utilized. However, the number of fabric support strips 230 should be limited such as not to increase the profile (e.g. diameter) of stent-graft prosthesis 200 an undesired amount. Thus, in preferred embodiments, 2 to 8 fabric supports strips 230 are utilized. In other preferred embodiments, 2 to 4 fabric support strips are utilized. Further, fabric support strips 230 need not be spaced equally about a circumference of inner PTFE layer 240. In preferred embodiments, a fabric support strip 230 does not extend around the entire circumference of inner PTFE layer 240.

In the embodiment shown in FIGS. 6-7, fabric support strips 230 are disposed between helical stent 220 and outer PTFE layer 210. However, this is not meant to limit the design and other configurations may be utilized. For example, and not by way of limitation, fabric support strips 230 may be disposed between helical stent 220 and inner PTFE layer 240.

FIGS. 9-14 show schematically some steps in an embodiment of a method of manufacturing or forming a stent-graft prosthesis, such as stent-graft prosthesis 100. Although described herein with stent-graft prosthesis 100, it will be apparent to one of ordinary skill that methods described herein may be utilized to form a stent-graft prosthesis according to any embodiment described herein, such as, for example, stent-graft prosthesis 200.

Figure 9:
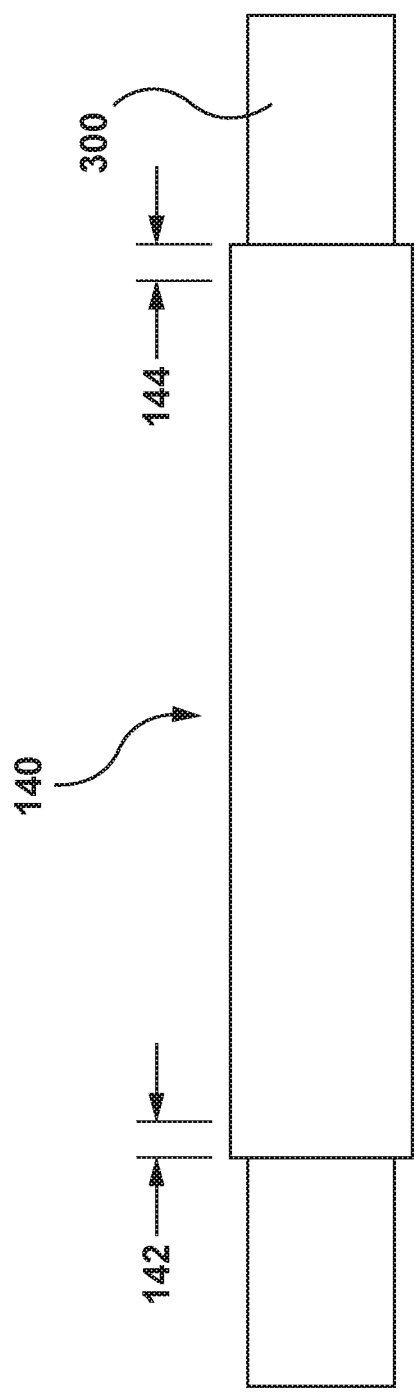

In the method, inner PTFE layer 140 is positioned over a mandrel 300, as shown in FIG. 9. As previously described, the length of inner PTFE layer 140 may be greater than the desired length of stent-graft prosthesis 100, because inner PTFE layer 140 includes first and second ends 142, 144 which may folded over or cuffed during the manufacturing process as will be explained in more detail herein. Thus, the length of inner PTFE layer 140 may be equal to the desired length of stent-graft prosthesis 100 plus the length of first and second ends 142, 144. In order to place inner PTFE layer 140 onto mandrel 300, as well as additional layers of material slid over mandrel 300, mandrel 300 may include a tapered expansion tip (not shown) to ease or assist in positioning of tubing over the mandrel. Inner PTFE layer 140 is slid over mandrel 300 until it is approximately centered thereon, as shown in FIG. 9.

Figure 10:
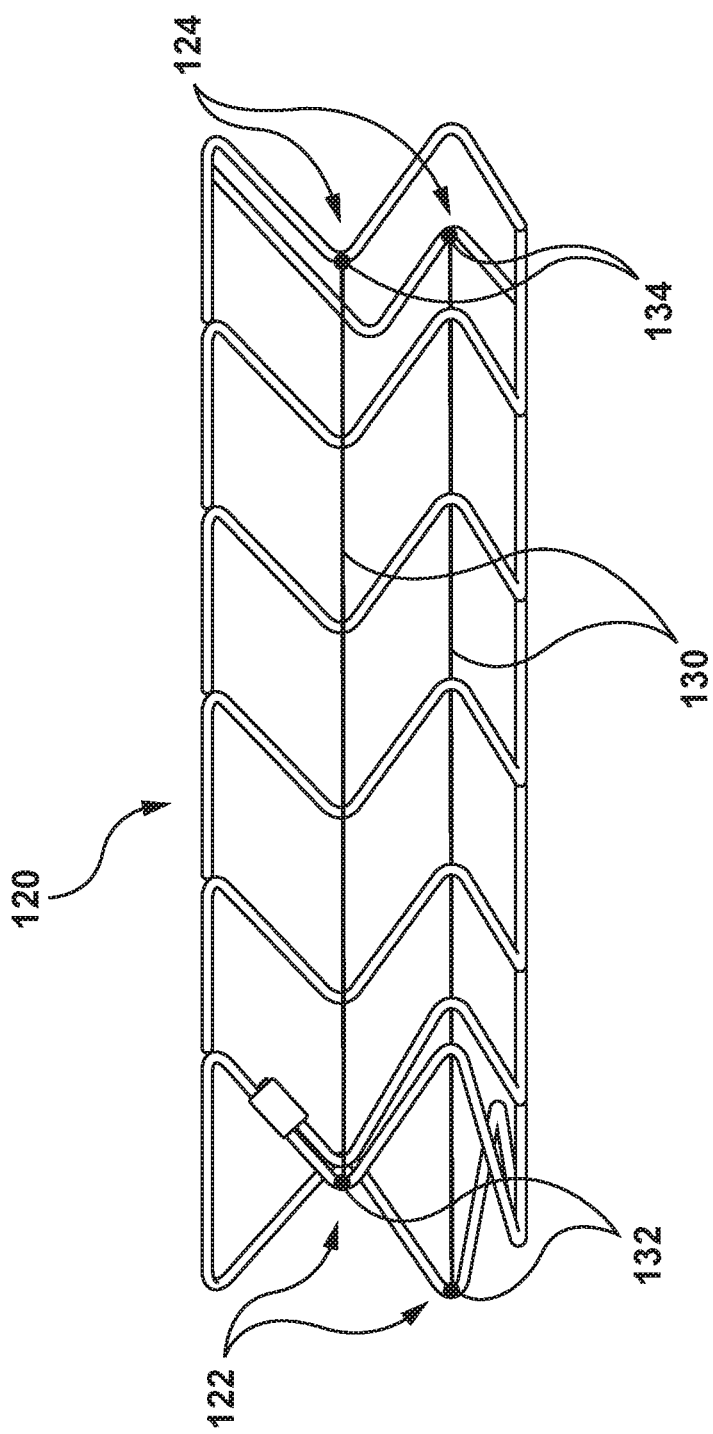

In another step of the method, each suture first end 132 of each suture 130 is coupled to stent first end 122, and each suture second end 134 of each suture 130 is coupled to stent second end 124 such that each suture 130 extends generally longitudinally from stent first end 122 to stent second end 124 of helical stent 120, as shown in FIG. 10.

Figure 11:
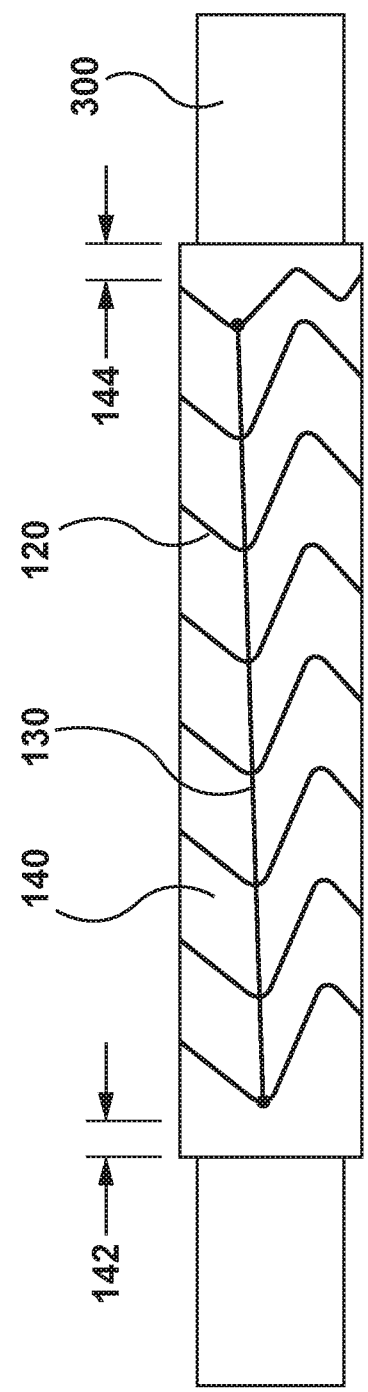

Once inner PTFE layer 140 is in place and sutures 130 have been coupled to helical stent 120 as described above, helical stent 120 is positioned over inner PTFE layer 140, as shown in FIG. 11. Helical stent 120 is not positioned on first and second ends 142, 144 of inner PTFE layer 140 because the ends are folded over or cuffed in a later processing step as described in more detail with respect to FIG. 13. Although the method is described with sutures 130 being coupled to helical stent 120 prior to placement of helical stent 120 over inner PTFE layer 140, this disclosure is not so limited. For example, and not by way of limitation, the sutures 130 may be coupled to helical stent 120 after helical stent 120 is position over inner PTFE layer 140.

Similarly, if the method is used to form stent-graft prosthesis 200, fabric support strips 230 may be placed over inner PTFE layer 240, and then helical stent 220 may be placed over fabric support strips 230. Alternatively, helical stent 220 may be placed over inner PTFE layer 240, and then fabric supports strips 230 may be placed over helical stent 220. In another non-limiting example, some fabric support strips 230 may be placed over inner PTFE layer 240 before helical stent 220, and other may be placed over helical stent 220.

Figure 12:
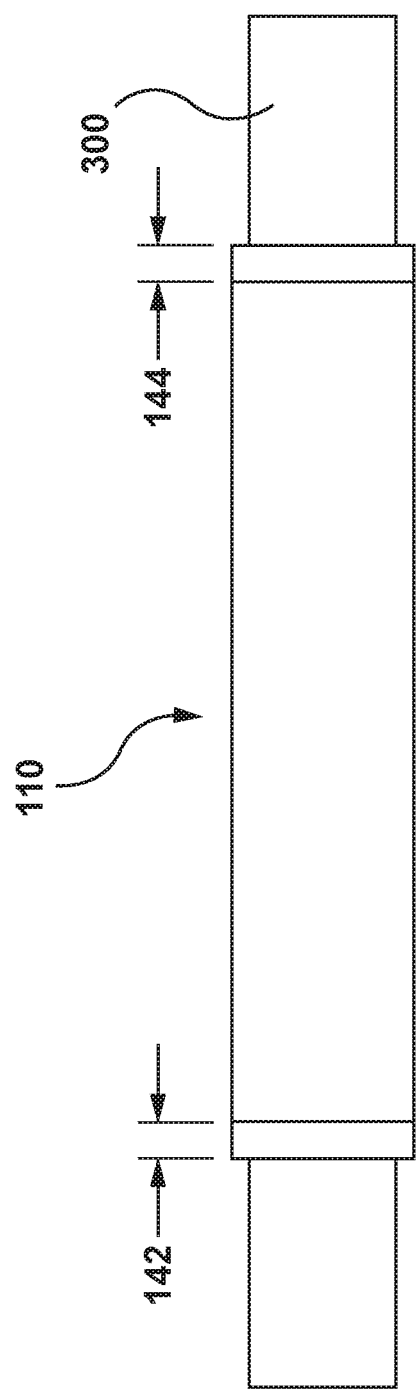
Figure 13:
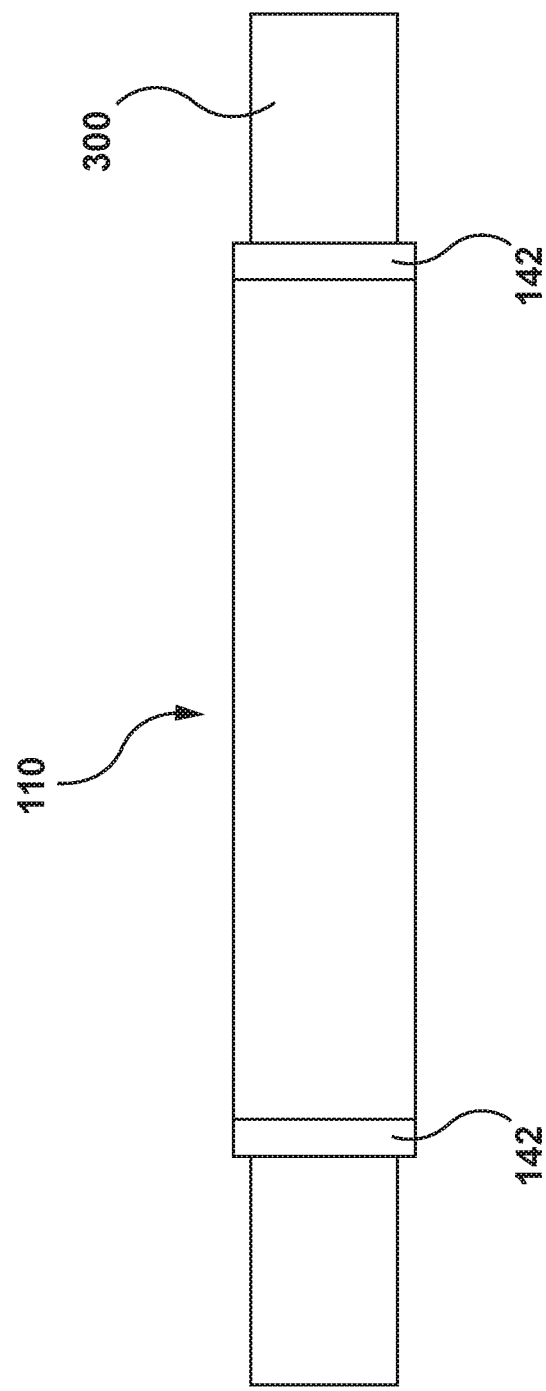

Once helical stent 120 is in place, outer PTFE layer 110 is then positioned directly over inner PTFE layer 140 and helical stent 120, as shown in FIG. 12. In an embodiment, the length of outer PTFE layer 110 is approximately equal to the desired length of stent-graft prosthesis 100. Outer PTFE layer 110 is slid over inner PTFE layer 140 until it is approximately centered thereon, as shown in FIG. 12, such that outer PTFE layer 110 is not positioned on first and second ends 142, 144 of inner PTFE layer 140. As shown in FIG. 13, first and second ends 142, 144 are then folded over or cuffed. More particularly, first and second ends 142, 144 are folded or rolled over such that an outer surface of first and second ends 142, 144 lays against or overlaps onto a portion of an outer surface of outer PTFE layer 110, thereby forming cuffs having three layers of ePTFE on the ends of the assembled components or layers. In one embodiment, first and second ends 142, 144 may each be approximately 5 mm in length.

Once outer PTFE layer 110 is in place, a heat shrink tubing 310 is slid over outer PTFE layer 110 until it is approximately centered thereon, as shown in FIG. 14. As will be understood by one of ordinary skill in the art, heat shrink tubing 310 is expanded tubing that will shrink when heat is applied thereto in an effort to return or recover to the relaxed diameter it originally had when extruded. When heat shrink tubing 310 shrinks or recovers, it radially compresses the assembled components or layers during the heating step described herein to form stent-graft prosthesis 100 in a radially compressed or delivery configuration suitable for delivery into the vasculature. The length of heat shrink tubing 310 may be greater than the length of outer PTFE layer 110 such that heat shrink tubing 310 completely/fully covers or extends over the assembled components or layers on mandrel 300. Heat shrink tubing 310 may include one or more slits or cuts 320, formed or made transverse to a longitudinal axis of heat shrink tubing 310, at a first and/or second end or edge 312, 314 thereof, to facilitate the step of removing the heat shrink material as will be described in more detail herein. Heat shrink tubing 310 may be formed of a polymeric material such as polytetrafluoroethylene (PTFE) and may include a coating coupled to or on an inner surface thereof. In one embodiment, the coating is high temperature resistant parylene HT (high temperature), commercially available from Specialty Coatings Systems of Indianapolis, Ind., which prevents bonding/adhesion between outer PTFE layer 110 (not shown in FIG. 14) and heat shrink tubing 310 during the heating step described herein. The parylene HT coating has a thickness not greater than five microns or micrometers in order to conform to the inner surface of heat shrink tubing 310, and in one embodiment, the parylene HT coating has a thickness not greater than one micron or micrometer.

With inner and outer PTFE layers 140, 110, helical stent 120, and heat shrink tubing 310 assembled onto mandrel 300, the assembly is heated such that the nodes and fibrils of inner and outer PTFE layers 140, 110 entangle, intertwine, interweave, or otherwise mesh together, thereby coupling inner and outer PTFE layers 140, 110 together. The heating step may be performed in any manner known to those skilled in the art. For example, and not by way of limitation, the assembled layers on mandrel 300 may be heated in an oven or similar device. In another non-limiting example, direct heating elements may be placed within a lumen (not shown) of mandrel 300, or surrounding mandrel 300 in close proximately thereto. Other heating methods and devices may also be used.

Once inner and outer PTFE layers 140, 110 are entangled or coupled together, stent-graft prosthesis 100 is thereby formed. Heat shrink tubing 310 may then be removed. In one embodiment, heat shrink tubing 310 may be ripped or torn off stent-graft prosthesis 100 by pulling at slits 320 formed therein. When heat shrink tubing 310 includes a parylene HT coating on the inner surface thereof as described above, heat shrink tubing 310 advantageously cracks or snaps apart during removal thereof. After heat shrink tubing 310 is removed, stent-graft prosthesis 100 may also be removed from mandrel 300 by pulling or sliding it off.

In addition, although the embodiment described above with respect to FIGS. 9-14 illustrates each of inner and outer PTFE layers 140, 110 as tubular components, it will be understood by those of ordinary skill in the art that inner and outer PTFE layers 140, 110 may be formed via PTFE material which is not originally formed as a tubular component.

Further, although the embodiment described above with respect to FIGS. 9-14 illustrates each of inner and outer PTFE layers 140, 110 as single tubular components, it will be understood by those of ordinary skill in the art that inner PTFE layer 140 may include one or more tubular PTFE layers or components and/or outer PTFE layer 110 may include one or more tubular ePTFE layers or components. If more than two layers of PTFE are included, the heating step as described herein operates to entangle all layers of PTFE together within the above-described waiting periods such that all of the PTFE layers, helical stent 120, and sutures 130 form stent-graft prosthesis 100.

While only some embodiments have been described herein, it should be understood that it has been presented by way of illustration and example only, and not limitation. Various changes in form and detail can be made therein without departing from the spirit and scope of the invention, and each feature of the embodiments discussed herein, and of each reference cited herein, can be used in combination with the features of any other embodiment. All patents and publications discussed herein are incorporated by reference herein in their entirety.

What is claimed is:

1. A stent-graft prosthesis comprising:
  a generally tubular outer PTFE layer, the outer PTFE layer defining an outer layer lumen therein;
  a generally tubular helical stent formed from a continuous wire wrapped in a helical pattern, the helical stent disposed within the outer layer lumen, the helical stent including a stent first end and a stent second end, and defining a stent lumen therein;
  a generally tubular inner PTFE layer disposed within the stent lumen defining an inner layer, therein; and
  a suture having a suture first end coupled to the stent first end and a suture second end coupled to the stent second end, wherein the suture is disposed between the outer PTFE layer and the inner PTFE layer,
  wherein the helical stent includes a plurality of bands, wherein adjacent bands of the helical stent are coupled to each other only through the continuous wire, the inner and outer PTFE layers, and the suture.

2. The stent-graft prosthesis of claim 1, wherein the suture comprises a plurality of sutures.

3. The stent-graft prosthesis of claim 2, where in the plurality of sutures are spaced equally around a circumference of the inner PTFE layer.

4. The stent-graft prosthesis of claim 1, wherein the suture is disposed between the inner PTFE layer and the helical stent.

5. The stent-graft prosthesis of claim 1, wherein the suture is disposed between the outer PTFE layer and the helical stent.

6. The stent-graft prosthesis of claim 1, wherein the suture is woven over and under the helical stent and is disposed between the inner PTFE layer and the outer PTFE layer.

7. The stent-graft prosthesis of claim 1, wherein the suture extends generally longitudinally.

8. The stent-graft prosthesis of claim 1, wherein the continuous wire of the helical stent includes a plurality of struts separated by apices, wherein the suture wraps entirely around a plurality of the apices as the suture extends from the stent first end to the stent second end.

9. A stent-graft prosthesis comprising:
  a generally tubular outer PTFE layer, the outer PTFE layer defining an outer layer lumen therein;
  a generally tubular helical stent formed from a continuous wire formed into a waveform having struts separated by apices and the waveform wrapped in a helical pattern, the helical stent disposed within the outer layer lumen, the helical stent including a stent first end and a stent second end, and defining a stent lumen therein;
  a generally tubular inner PTFE layer disposed within the stent lumen defining an inner layer, therein; and
  a suture having a suture first end coupled to the stent first end and a suture second end coupled to the stent second end, wherein the suture is disposed between the outer PTFE layer and the inner PTFE layer, and wherein the suture wraps entirely around a plurality of the apices as the suture extends from the stent first end to the stent second end.

10. The stent-graft prosthesis of claim 9, wherein the suture comprises a plurality of sutures.

11. The stent-graft prosthesis of claim 10, where in the plurality of sutures are spaced equally around a circumference of the inner PTFE layer.

12. The stent-graft prosthesis of claim 9, wherein the suture is disposed between the inner PTFE layer and the helical stent.

13. The stent-graft prosthesis of claim 9, wherein the suture is disposed between the outer PTFE layer and the helical stent.

14. The stent-graft prosthesis of claim 9, wherein the suture extends generally longitudinally.

15. The stent-graft prosthesis of claim 9, wherein the helical stent includes a plurality of bands, wherein adjacent bands of the helical stent are coupled to each other only through the continuous wire, the inner and outer PTFE layers, and the suture.

* * * * *